US009915737B2

(12) United States Patent
Grobshtein et al.

(10) Patent No.: US 9,915,737 B2
(45) Date of Patent: Mar. 13, 2018

(54) SYSTEMS AND METHODS FOR IMAGING WITH MULTI-HEAD CAMERA

(71) Applicant: General Electric Company, Schenectady, NY (US)

(72) Inventors: Yariv Grobshtein, Tirat Carmel (IL); Jean-Paul Bouhnik, Tirat Carmel (IL); Gil Kovalski, Tirat Carmel (IL); Shiran Golan, Haifa (IL)

(73) Assignee: General Electric Company, Schenectady, NY (US)

( * ) Notice: Subject to any disclaimer, the term of this patent is extended or adjusted under 35 U.S.C. 154(b) by 40 days.

(21) Appl. No.: 15/086,913

(22) Filed: Mar. 31, 2016

(65) Prior Publication Data

US 2017/0090040 A1   Mar. 30, 2017

Related U.S. Application Data

(63) Continuation-in-part of application No. 14/871,091, filed on Sep. 30, 2015, now Pat. No. 9,579,072.

(51) Int. Cl.
G01T 1/164   (2006.01)

(52) U.S. Cl.
CPC .................. G01T 1/164 (2013.01)

(58) Field of Classification Search
CPC ....................................... G01T 1/164
See application file for complete search history.

(56) References Cited

U.S. PATENT DOCUMENTS

| 5,025,376 | A | * | 6/1991 | Bova | A61N 5/1048 250/385.1 |
| 9,029,791 | B1 | * | 5/2015 | Kovalski | A61B 6/037 250/369 |
| 9,470,967 | B1 | * | 10/2016 | Vorst | G03B 21/606 |
| 2002/0149305 | A1 | * | 10/2002 | Danielsson | A61N 5/1048 313/105 CM |

(Continued)

OTHER PUBLICATIONS

U.S. Appl. No. 14/788,180, entitled "Systems and Methods for Dynamic Scanning With Multi-Head Camera," filed Jun. 30, 2015; 49 pages.

(Continued)

*Primary Examiner* — Casey Bryant
(74) *Attorney, Agent, or Firm* — Dean D. Small; The Small Patent Law Group, LLC

(57) ABSTRACT

A nuclear medicine (NM) multi-head imaging system is provided that includes a gantry defining a bore configured to accept an object to be imaged. The imaging system includes a plurality of detector units coupled to the gantry, with each of the detector units having a respective detector field-of-view (FOV). Each of the detector units is configured to rotate about a respective unit axis, with the plurality of detector units including at least a first and a second detector unit. The imaging system also includes at least one processor configured to execute programmed instructions stored in memory, wherein the at least one processor, when executing the programmed instructions, rotates the first and second detector units as the first and second detector units acquire persistence image data; and generates at least one persistence image based on the persistence image data.

17 Claims, 7 Drawing Sheets

(56) References Cited

U.S. PATENT DOCUMENTS

| | | | |
|---|---|---|---|
| 2005/0265515 A1* | 12/2005 | Tashiro | A61B 6/032 378/20 |
| 2009/0099563 A1* | 4/2009 | Ciaccio | A61B 5/1075 606/41 |
| 2010/0001197 A1* | 1/2010 | Aoyama | A61B 6/06 250/370.09 |
| 2015/0094573 A1 | 4/2015 | Bouhnik et al. | |
| 2015/0177939 A1 | 6/2015 | Anderson et al. | |
| 2016/0183919 A1* | 6/2016 | Amthauer | A61B 5/0035 345/419 |

OTHER PUBLICATIONS

Bellevre et al.; First determination of the heart-to mediastinum radio using cardiac dual isotope (123 I-MIBG/ 99m Tc-tetrofosmin) CZT imaging in patients with heart failure; the ADRECARD study;Eur J. Nucl. Med. Mol. Imaging; Jul. 31, 2015; 8 pages.

* cited by examiner

SYSTEMS AND METHODS FOR IMAGING WITH MULTI-HEAD CAMERA

The present application claims priority to, and is a continuation-in-part application of U.S. patent application Ser. No. 14/871,091, filed Sep. 30, 2015, and entitled "Systems and Methods for Imaging with Multi-Head Camera," the subject matter of which is hereby incorporated in its entirety.

BACKGROUND

The subject matter disclosed herein relates generally to imaging systems, and more particularly to nuclear medical imaging systems having multi-head detectors.

In nuclear medicine (NM) imaging, such as single photon emission computed tomography (SPECT) or positron emission tomography (PET) imaging, radiopharmaceuticals are administered internally to a patient. The radiopharmaceuticals emit radiation that may be captured by an NM imaging system to generate images for diagnostic review. The NM imaging system may be configured as a multi-head system having a number of individual detectors (or gamma cameras) that are distributed about a bore of the gantry. The detectors are spaced apart from each other such that gaps exist between adjacent detectors. Each detector may be configured to move to provide a range over which the detector may acquire image data.

Prior to the imaging session in which the diagnostic images are obtained, the patient is positioned relative to the detectors so that a collective field-of-view of the NM imaging system includes the anatomical region of interest (e.g., heart, brain, etc.). At this time, one or more persistence images may be obtained and reviewed to position the patient. The persistence images are typically only used to position the patient and, as such, have a lower quality than the images used for diagnosis. As the images are acquired, the technician reviews the images and incrementally moves the patient within the bore of the gantry so that the anatomical region-of-interest is within the collective field-of-view. It is generally desirable to quickly position the patient, because the emissions from the radioisotopes reduce over time. During the time in which persistence images are acquired, a technician may also assess the activity of the radioisotopes for determining the scan duration It can be challenging, however, to use persistence images from multi-head imaging systems. For example, gaps may exist between adjacent detectors thereby rendering it more difficult to identify the anatomical region of interest in the persistence images. This process may be made even more difficult for field-of-views that are only slightly larger than the anatomical region of interest.

BRIEF DESCRIPTION

In an embodiment, a nuclear medicine (NM) multi-head imaging system is provided that includes a gantry defining a bore configured to accept an object to be imaged. The imaging system includes a plurality of detector units coupled to the gantry, with each of the detector units having a respective detector field-of-view (FOV). Each of the detector units is configured to rotate about a respective unit axis, with the plurality of detector units including at least a first detector unit and a second detector unit. The imaging system also includes at least one processor configured to execute programmed instructions stored in memory, wherein the at least one processor, when executing the programmed instructions, rotates the first and second detector units as the first and second detector units acquire persistence image data; and generates at least one persistence image based on the persistence image data.

In an embodiment, a method of imaging an object within a bore of a nuclear medicine (NM) imaging system is provided. The NM imaging system includes a plurality of detector units that are distributed about the bore and include a detector field-of-view (FOV). The plurality of detector units includes at least a first detector unit and a second detector unit. The method includes rotating the first detector unit and rotating the second detector unit (e.g., about respective unit axes). The method also includes acquiring persistence image data with the first and second detector units while rotating the first and second detector units. Further, the method includes generating at least one persistence image using the persistence image data.

In an embodiment, a tangible and non-transitory computer readable medium is provided. The tangible and non-transitory computer readable medium includes one or more software modules configured to direct one or more processors to rotate a first detector unit; rotate a second detector unit, wherein the first and second detector units are disposed about a bore of a gantry; acquire persistence image data with the first and second detector units while rotating the first and second detector units; and generate at least one persistence image using the persistence image data.

DETAILED DESCRIPTION

Figure 1:
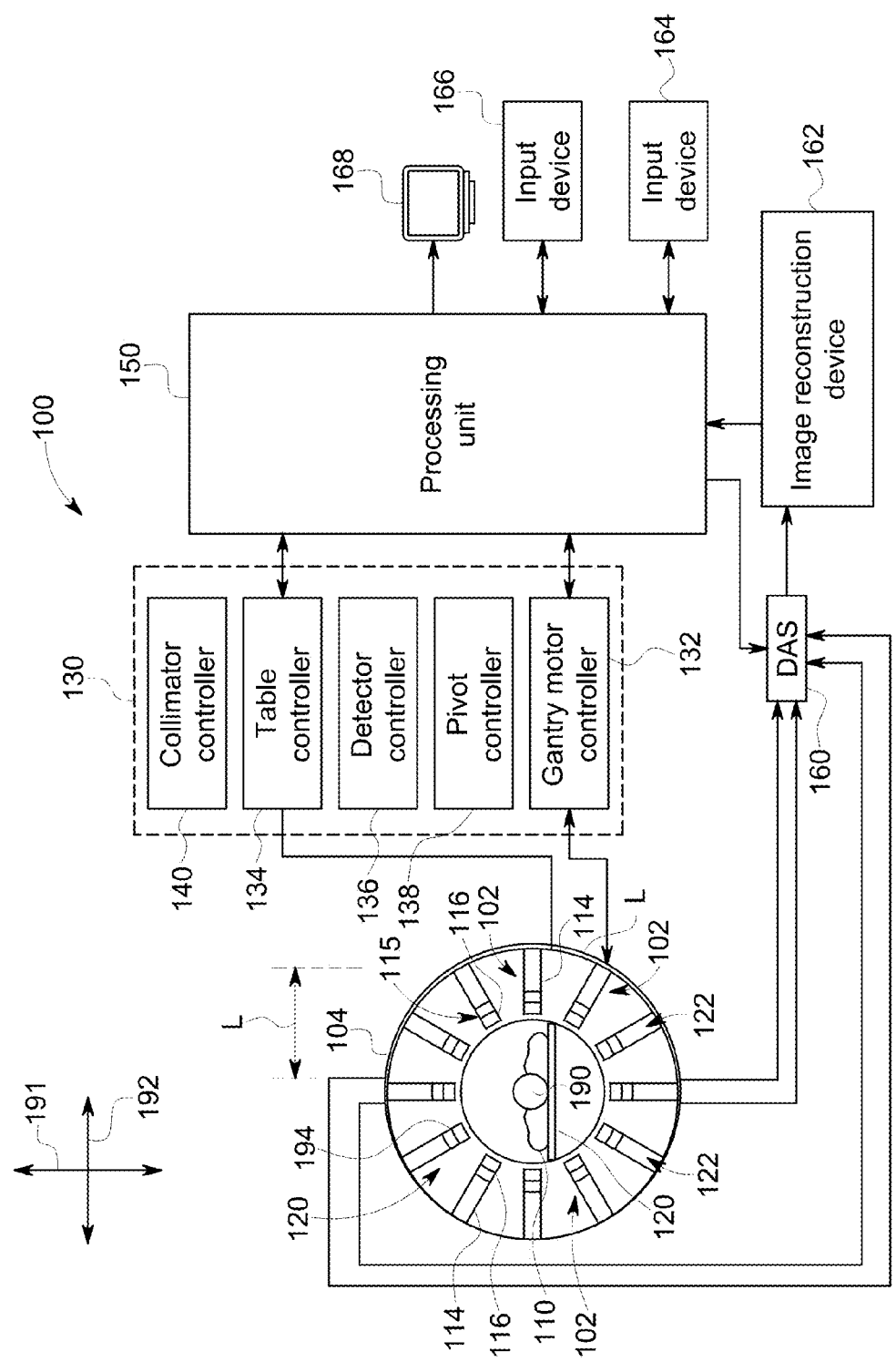
FIG. 1 provides a schematic view of a nuclear medicine (NM) imaging system in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, phrases such as "a plurality of [elements]" and the like, when used in the description and claims, do not necessarily refer to each and every element that a system may have. The system may have other elements that are similar to the plurality of elements but do not have the same features or limitations. For example, the phrase "a plurality of detector units [being/having a recited feature or limitation]" does not necessarily mean that each and every detector unit of the system has the recited feature or limitation. Other detector units may not include the recited feature or limitation. Similarly, phrases such as "each of the detector units [being/having a recited feature or limitation]" and the like, when used in the description and claims, does not preclude the possibility that the system may have other detector units. Accordingly, unless explicitly stated otherwise (e.g., "each and every detector unit of the system"), embodiments may include similar elements that do not have the recited features or limitations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Embodiments set forth herein include nuclear medicine (NM) multi-head imaging systems, which are hereinafter referred to as NM imaging systems, methods of acquiring NM images, and/or computer readable media having one or more software modules that direct one or more processors to execute the methods described herein. Embodiments described herein and illustrated by the figures may be implemented in imaging systems, such as, for example, single photon emission computed tomography (SPECT), SPECT computed tomography (SPECT-CT), positron emission tomography (PET), and PET-CT.

In order to verify the correctness or acceptability of a patient position, for example a position within a bore of a multi-head detector system, a fast technique is desired to determine a patient contour based on emission data (e.g., from a patient that has been administered a radiopharmaceutical. Various embodiments utilize a sweeping acquisition mode to identify the contour in a panoramic view mode.

It may be noted that in various embodiments, a fully populated (e.g., detectors positioned around an entire circumference of a bore) detector arrangement may be utilized, while in other embodiments, a partially populated (e.g., detectors positioned around less than an entire circumference of a bore, such as 180° or 270°, or detectors positioned about a circumference with certain detectors idle or otherwise not used) may be utilized. In some embodiments, a gantry may be rotated to acquire additional information, for example from angles at which no detectors of a partially populated system are initially oriented. Even with a fully populated arrangement, a gantry may be rotated to provide desired additional or alternative angles or lines of sight.

It may also be noted that, in various embodiments, persistence images may be used for positioning in an in-out direction (e.g., along the length of the patient). As the acquisition for persistence imaging is relatively fast, the amount of noise in each image may be relatively high in comparison to imaging information acquired. Various techniques (e.g., post-processing methods) may be utilized to improve persistence images and/or reduce the effects of noise. For example, views that look on to the same or similar area or volume of the object from opposite directions may be summed. As another example, views which look on to the same or similar area from the same or similar angle may be summed. As another example, filtering may be applied to reduce noise. As one more example, information from multiple pixels may be combined together, for instance by creating a new image where each pixel in the new image is an average of a larger area (e.g., 2 pixel×2 pixel) area in an original image.

A technical effect of at least one embodiment may provide improved persistence imaging (e.g., improved accuracy and/or reduced amount of acquisition time). A technical effect of at least one embodiment may provide a fast technique to determine the contour of an object to be imaged without use of an external device, such as a CT scanner.

FIG. 1 provides a schematic view of a nuclear medicine (NM) multi-head imaging system 100 in accordance with various embodiments. Generally, the imaging system 100 is configured to acquire imaging information (e.g., photon counts) from an object to be imaged (e.g., a human patient) that has been administered a radiopharmaceutical.

It should be noted that the arrangement of FIG. 1 is provided by way of example for illustrative purposes, and that other arrangements may be employed in various embodiments. In the illustrated example, the imaging system 100 includes a plurality of detector assemblies 102 that are coupled (e.g., mounted) to a gantry 104 that defines a bore 118 of the imaging system 100. The imaging system 100 may also include a table 120 that is positioned within the bore 118. The table 120 is configured to support an object 110, such as a patient. The detector assemblies 102 are positioned circumferentially about the bore 118. The detector assemblies 102 may be positioned within the gantry 104 such that the detector assemblies 102 are not visible to the patient or, alternatively, at least a portion of the detector assemblies 102 may be exposed within the bore 118.

In the illustrated embodiment, each detector assembly 102 includes an arm 114 and a head 116. The head 116 includes at least one detector unit 115. The head 116 is disposed at a radially inward end of the arm 114. The arm 114 is configured to move the head 116 radially toward and/or away from a center of the bore 118 (and/or in other directions) and thereby move the corresponding detector unit(s) 115. A detector unit 115 may have a relative position with respect to the bore 118 or a central longitudinal axis 190 that extends through the bore 118. The longitudinal axis 190 may be understood as corresponding to an in-out direction. The relative position may include a spatial location (e.g., coordinates in an X, Y, Z space) and an orientation (e.g., rotational position or orientation). For example, the relative position of each detector unit 115 may be defined by (1) a rotational orientation or position of the plurality of detector units 115; (2) a radial position of the corresponding detector unit 115; and (3) a rotational position or orientation of the corresponding detector unit 115.

Each of (1), (2), and (3) may be identified or determined by the imaging system. To this end, the imaging system and/or the detector units may include encoders that identify (1), (2), or (3). For example, each of the arms 114 may include or be operably coupled to a motor that selectively controls the position of the head 116 relative to the bore 118. When the head 116 is moved, information relating to the state of the motor may identify the radial position of the detector unit. As another example, each of the detector units 115 may be secured to a common ring (not show) that is capable of rotating about the longitudinal axis 190. An encoder may identify the rotational position of the ring (e.g., in degrees or radians) that may be used to identify the relative position of each of the detector units. As another example, the head 116 may be configured to pivot or rotate about a unit axis 194. The head 116 may be operably coupled to a motor that selectively controls the rotational position of the head 116. When the head 116 is rotated, information relating to the state of the motor may identify the rotational position of the corresponding detector unit.

The detector unit 115 may be, for example, a semiconductor detector. For example, a semiconductor detector in various embodiments may be constructed using different materials, such as semiconductor materials, including Cadmium Zinc Telluride (CdZnTe), often referred to as CZT, Cadmium Telluride (CdTe), and Silicon (Si), among others. The detector unit 115 may be particularly configured for use with, for example, nuclear medicine (NM) imaging systems, positron emission tomography (PET) imaging systems, and/or single photon emission computed tomography (SPECT) imaging systems.

Each of the detector units 115 in various embodiments is smaller than a conventional whole body or general purpose imaging detector. A conventional imaging detector may be large enough to image most or all of a width or length of a patient's body at one time and may have a diameter or a larger dimension of approximately 50 cm or more. In contrast, each of the detector units 115 may have dimensions of, for example, 4×20 cm and may be formed of Cadmium Zinc Telluride (CZT) tiles or modules. As another example, each of the detector units 115 may be 8×8 cm in size and be composed of a plurality of CZT pixelated modules (not shown). For example, each module may be 4×4 cm in size and have 16×16=256 pixels (pixelated anodes). In some embodiments, each detector unit 115 includes a plurality of modules, such as an array of 1×7 modules. However, different configurations and array sizes are contemplated including, for example, detector units 115 having multiple rows of modules.

Each of the detector units 115 has a detector surface or face, which is directed towards the object 110 or an (ROI) within the object 110. It should be understood that the detector units 115 may be different sizes and/or shapes with respect to each other, such as square, rectangular, circular or other shape. An actual FOV of each of the detector units 115 may be directly proportional to the size and shape of the respective detector unit. The detector units 115 are arranged in a set or array 120. The set 120 may be rotated as a group about the bore 118 or, more specifically, about the longitudinal axis 190. Accordingly, each of the detector units 115 may be selectively rotated about the longitudinal axis 190, selectively moved radially toward or away from the longitudinal axis 190, and be selectively rotated about a respective unit axis 194 that extends parallel to the longitudinal axis 190. As used herein, an element or component is "selectively rotatable," "selectively movable," and the like if the element or component may be controlled in a manner that is different with respect to similar elements or components. For example, one detector unit may be rotated 15° about its respective unit axis and another detector unit may be rotated 10° about its respective unit axis. The phrases do not require, however, the each element or component be controlled differently. Instead, the terms "selective" or "selectively" only acknowledge that the element or component may be controlled differently.

The detector units 115 may be utilized to acquire imaging information for both persistence and diagnostic images. As used herein, a persistence image refers to an image that provides sufficient information for positioning a patient but not for diagnostic purposes. Persistence images may be used, for example, for positioning and/or quality control. For example, persistence image data may be sufficient to identify an edge of a patient (e.g., an edge of activity corresponding to radiotracer within the patient) but insufficient to differentiate individual organs or structures within the patient, or to perform a diagnosis based on an analysis of one or more organs or structures within the patient. Persistence image data accordingly may be acquired more quickly than diagnostic image data. In some embodiments, persistence image data may be acquired over a time period that is 10% or less than a time period used to acquire diagnostic image data. For example, persistence image data may be acquired over a time period of 30-60 seconds in some embodiments, while diagnostic image data may be acquired over a time period of 5-10 minutes. Further, in various embodiments, more detector units may be employed to acquire diagnostic image data than persistence image data.

For example, in various embodiments, a first detector unit and a second detector unit may be rotated or pivoted about respective unit axes 194 to collect persistence image data while being swept over a portion of an object (e.g., object 110) to be imaged, and at least one persistence image may be generated based on the acquired persistence image data from the first and second detector units. It may be noted that, in some embodiments, persistence image data may be used to generate a persistence image, and also later added to imaging data as part of generation of a diagnostic image.

The table 120 is configured with a support mechanism (not shown) to support and carry the object 110 in one or more of a plurality of viewing positions within the bore 118 and relative to the detector units 115. For example, the table 120 may be operably coupled to one or more motors (not shown). The motors may be configured to move the table 120 along the longitudinal axis 190 (e.g., for in-out adjustment), along an elevation axis 191 (e.g., for up-down adjustment), and also along a lateral axis 192 (e.g., for lateral or left-right adjustment). The axes 190-192 are mutually perpendicular. As such, the table 120 and the corresponding motors may selectively position the object 110 within the bore 118. As described above with respect to the detector units, an encoder or other device may determine a position of the table 120 within the bore 118.

In the illustrated embodiment, the gantry 104 is circular or donut-shaped. In other embodiments, however, the gantry 104 may be configured to have other shapes. For example, the gantry 104 may be formed as a closed ring or circle, or as an open arc or arch which allows the object 110 to be easily accessed while imaging and facilitates loading and unloading of the object 110. The gantry 104 may be rotated about the longitudinal axis 190.

Optionally, for embodiments employing one or more parallel-hole collimators, multi-bore collimators may be constructed to be registered with pixels of the detector units 115, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector areas near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the table 120, the detector units 115, the gantry 104 and/or the collimators 122. The controller unit 130 may have a gantry motor controller 132, a table controller 134, a detector controller 136, a pivot controller 138, and a collimator controller 140. The controllers 130, 132, 134, 136, 138, 140 may be automatically commanded by a processor (or processing unit) 150, manually controlled by an operator, or a combination thereof. The controllers 130, 132, 134, 136, 138, 140 may be part of a processing unit 150.

In various embodiments the processing unit 150 includes processing circuitry configured to perform one or more tasks, functions, or steps discussed herein. It may be noted that "processing unit" as used herein is not intended to necessarily be limited to a single processor or computer. For example, the processing unit 150 may include multiple processors, ASIC's and/or computers, which may be integrated in a common housing or unit, or which may distributed among various units or housings. It may be noted that operations performed by the processing unit 150 (e.g., operations corresponding to process flows or methods discussed herein, or aspects thereof) may be sufficiently complex that the operations may not be performed by a human being within a reasonable time period.

The processing unit 150 includes a memory (e.g., a tangible and non-transitory memory). It may be noted that other types, numbers, or combinations of modules, units, or controllers may be employed in alternate embodiments, and/or various aspects of modules, units, or controllers described herein may be utilized in connection with different modules, units, or controllers additionally or alternatively. Generally, the various aspects of the processing unit 150 act individually or cooperatively with other aspects to perform one or more aspects of the methods, steps, or processes discussed herein. The memory may include one or more computer readable storage media. Further, the process flows and/or flowcharts discussed herein (or aspects thereof) may represent one or more sets of instructions that are stored in the memory for direction of operations of the imaging system 100.

In the illustrated embodiment, the processing unit 150 controls the detector units 115 to acquire persistence image data as well as diagnostic image data. The processing unit 150 (e.g., via a controller forming a part of the processing unit 150 or associated with the processing unit 150) for example may pivot or sweep one or more detector units 115 about corresponding unit axis 194 (or axes 194) during acquisition of image data. The processing unit 150 may control one or more detector units to acquire more information during diagnostic data acquisition than during persistence data acquisition.

The gantry motor controller 132 may move the detector units 115 with respect to the object 110, for example, individually, in segments or subsets, or simultaneously in a fixed relationship to one another. For example, in some embodiments, the gantry controller 132 may cause the detector units 115 and/or support members to move relative to or rotate about the object 110, which may include motion of less than or up to 180° (or more).

The table controller 134 may move the table 120 to position the object 110 relative to the detector units 115. The table 120 may be moved in up-down directions along the elevation axis 191, in-out directions along the longitudinal axis 190, and right-left directions along the lateral axis 192, for example. The detector controller 136 may control movement of each of the detector units 115 to move together as a group or individually. The detector controller 136 also may control movement of the detector units 115 in some embodiments to move closer to and farther from a surface of the object 110, such as by controlling translating movement of the detector units 115 linearly towards or away from the object 110 (e.g., sliding or telescoping movement).

The pivot controller 138 may control the pivoting or rotating movement of the detector units 115. For example, one or more of the detector units 115 or heads 116 may be rotated or swept about a unit axis 194 to view the object 110 from a plurality of angular orientations to acquire, for example, image data for persistence images. The detector units 115 may also be selectively controlled to obtain diagnostic 3D image data in a 3D SPECT or 3D imaging mode of operation. The collimator controller 140 may adjust a position of an adjustable collimator, such as a collimator with adjustable strips (or vanes) or adjustable pinhole(s). The detector units 115 may be swept, rotated, or pivoted about corresponding unit axes 194 continuously in some embodiments, or as part of a series of steps in other embodiments. For example, in some embodiments, the processing unit 150 may be configured to rotate one or more detector units 115 within corresponding sweep ranges. The one or more detector units 115 may be incrementally moved to discrete rotational positions within the corresponding sweep range. It may be noted that, for persistence images, the edge of an object (or the edge of activity corresponding to an introduced radiotracer) may be of particular interest in positioning the object. Accordingly, the processing unit 150 may be configured to acquire a larger amount of persistence image data toward the edge of an object (e.g., an edge of radioactive activity in the object) than toward the middle of the object using the one or more detector units. For example, in some embodiments, the processing unit 150 may be configured to utilize smaller steps between rotational positions toward the edge of an object than are used toward the middle of the object. As another example, for embodiments where the detector units 115 are swept or pivoted about unit axes 194 continuously, the detector units 115 may be pivoted more rapidly when collecting data for the middle of the object and pivoted more slowly when collecting data for the edges of the object.

It may be noted that one or more aspects of image data acquisition may be varied for the persistence image data in comparison to when acquiring diagnostic image data. For example, more detector units 115 may be used to collect diagnostic image data than are used for persistence image data acquisition. A longer acquisition time may be used to collect diagnostic image data than is used for persistence image data acquisition. Additional sweep steps (and/or smaller sweep steps) and/or a slower sweep rate may be used to collect diagnostic image data than is used for persistence image data acquisition. As one more example, processing unit 150 may be configured to utilize different energy windows for persistence and diagnostic image data acquisition. For example, a broader energy window may be employed to identify counted events for persistence image data to include the number of counts and/or reduce acquisition time, while a narrower energy window may be employed to identify counted events for diagnostic image data to reduce noise and/or improve resolution.

It should be noted that motion of one or more detector units 115 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the object 110 or a portion of the object 110, the detector units 115, the gantry 104, the table 120 and/or the collimators 122 may be adjusted, such as to first or initial imaging positions, as well as subsequent imaging positions. The detector units 115 may each be positioned to image a portion of the object 110. Alternatively, for example in a case of a small size object 110, one or more of the detector units 115 may not be used to acquire data. Positioning may be accomplished manually by the operator and/or automatically, which may include using, for example, image data such as other images acquired before the current acquisition, such as by another imaging modality such as X-ray Computed Tomography (CT), MM, X-Ray, PET or ultrasound. In some embodiments, the additional information for positioning, such as the other images, may be acquired by the same system, such as in a hybrid system (e.g., a SPECT/CT system). Additionally, the detector units 115 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design.

After the detector units 115, the gantry 104, the table 120, and/or the collimators 122 are positioned, persistence image data may be acquired for generating one or more persistence images, for example to confirm that the object 110 is satisfactorily positioned. As the positioning is checked and appropriate adjustments are made, the detector units 115, the gantry 104, the table 120, and/or the collimators 122 may be positioned to acquire three-dimensional (3D) SPECT images. The image data acquired by each detector unit 115 may be combined and reconstructed into a composite image or 3D images in various embodiments.

In various embodiments, a data acquisition system (DAS) 160 receives electrical signal data produced by the detector units 115 and converts this data into digital signals for subsequent processing. However, in various embodiments, digital signals are generated by the detector units 115. An image reconstruction device 162 (which may be a processing device or computer) and a data storage device 164 may be provided in addition to the processing unit 150, or may form a portion of the processing unit 150. It should be noted that one or more functions related to one or more of data acquisition, motion control, data processing and image reconstruction may be accomplished through hardware, software, and/or by shared processing resources, which may be located within or near the imaging system 100, or may be located remotely. Additionally, a user input device 166 may be provided to receive user inputs (e.g., control commands), as well as a display 168 for displaying screens to the user. The DAS 160 receives the acquired image data from the detector units 115 together with the corresponding lateral, vertical (or elevational), rotational, and swiveling coordinates of the gantry 104, the detector units 115, and heads 116 for accurate reconstruction of images.

In various embodiments, the detector unit may include an array of pixelated anodes, and may generate different signals depending on the location of where a photon is absorbed in the volume of the detector under a surface of the detector. The volumes of the detector under the pixelated anodes are defined as voxels (not shown). For each pixelated anode, the detector has a corresponding voxel. The absorption of photons by certain voxels corresponding to particular pixelated anodes results in charges generated that may be counted. The counts may be correlated to particular locations and used to construct an image or a composite image.

Figure 2:
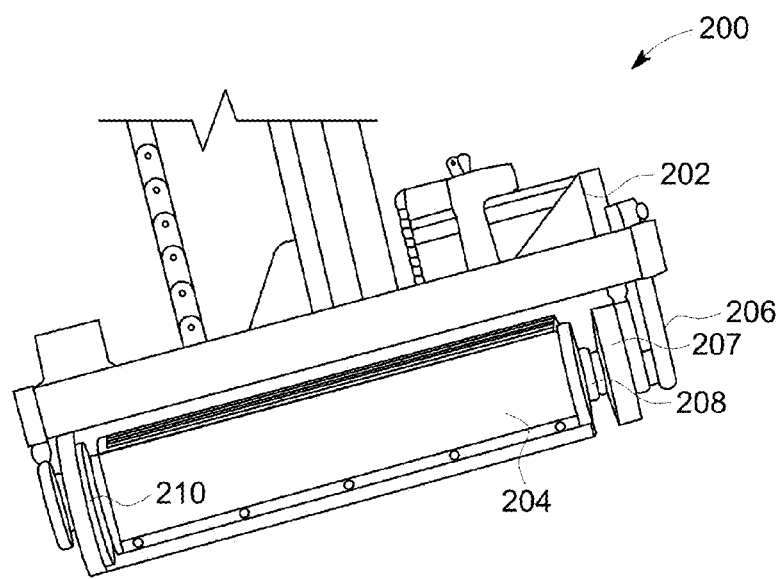
FIG. 2 provides a perspective view of a detector head in accordance with an embodiment.
Figure 3:
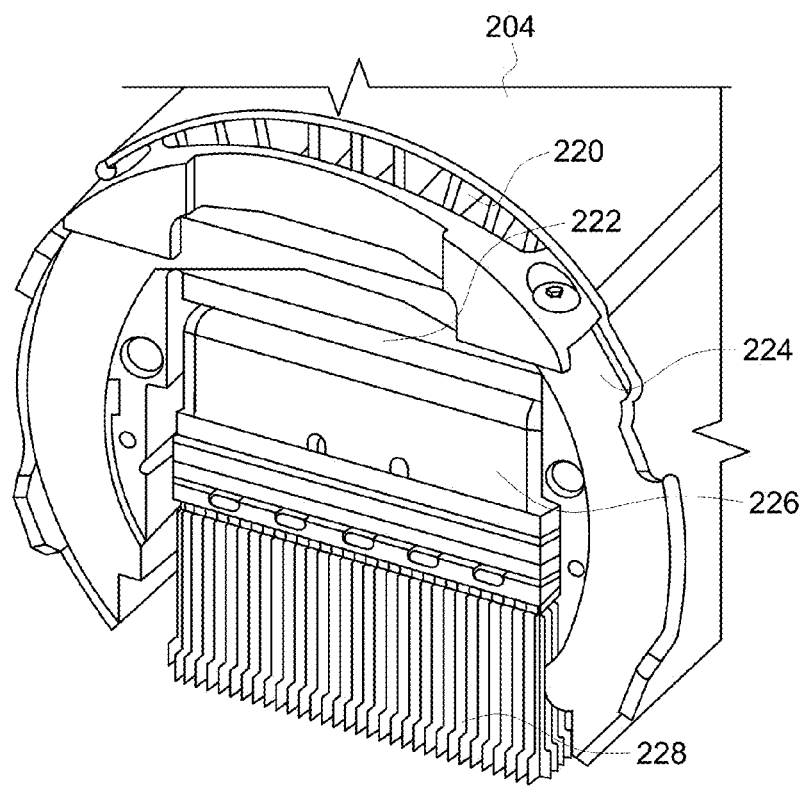
FIG. 3 shows a sectional view of the detector head of FIG. 2.

FIG. 2 is a perspective view of a detector head 200 formed in accordance with various embodiments, and FIG. 3 is a sectional view of the detector head 200. As shown in FIG. 2, the detector head 200 includes a stepper motor 202 that may be utilized to pivot a detector column 204. It may be noted that motors other than stepper motors may be used in various embodiments. Generally, "step-and-shoot" motion may be employed in various embodiments. In step-and-shoot motion, the detector is rapidly pivoted, and then remains stationary during data collection. Step-and-shoot motion may be utilized in various embodiments to eliminate or reduce power transients and/or other electronic noise associated with activation of electrical motors. Use of step-and-shoot motion may also be utilized to eliminate orientation uncertainties associated with each collected photon.

However, it may be noted that, in various embodiments, with fine orientation encoders, and frequent sampling of the orientation encoders, detector aiming may be associated with each detected photon to sufficient accuracy even if the detectors are continuously pivoting during data acquisition. The detector column 204, for example, may include a shield, a processing board, a detector (e.g., a CZT detector) and a collimator. The detector head 200 also includes a gear 206 coupling the stepper motor to the column 204, as well as a slip ring 207 (configured to allow for transfer of signals between the rotating detector column 204 and non-rotating components) and a multiplex board 208. In the illustrated embodiment, the detector head 200 also includes an air channel 210 configured to provide cooling to components of the detector head 200. Also shown in FIG. 3, the detector column 204 includes a heat sink 220, a printed circuit board 222 (which may incorporate one or more aspects of the processing unit 120), a lead shielding 224, a CZT detector module 226, and a collimator 228 that is registered to the CZT detector module 226 in the illustrated embodiment. Additional details and discussion regarding detector heads is provided in U.S. patent application Ser. No. 14/671,039, entitled "Reduced Airborne Contamination Detector Heads," filed Mar. 27, 2015, the subject matter of which is incorporated herein by reference in its entirety.

As described above, the image data acquired with different imaging arrangements may be acquired when the set of detector units are stationary. It is contemplated, however, that the image data may be acquired while the set of the detector units are moving. In such embodiments, the image data may be modified to compensate for the movement.

Figure 4:
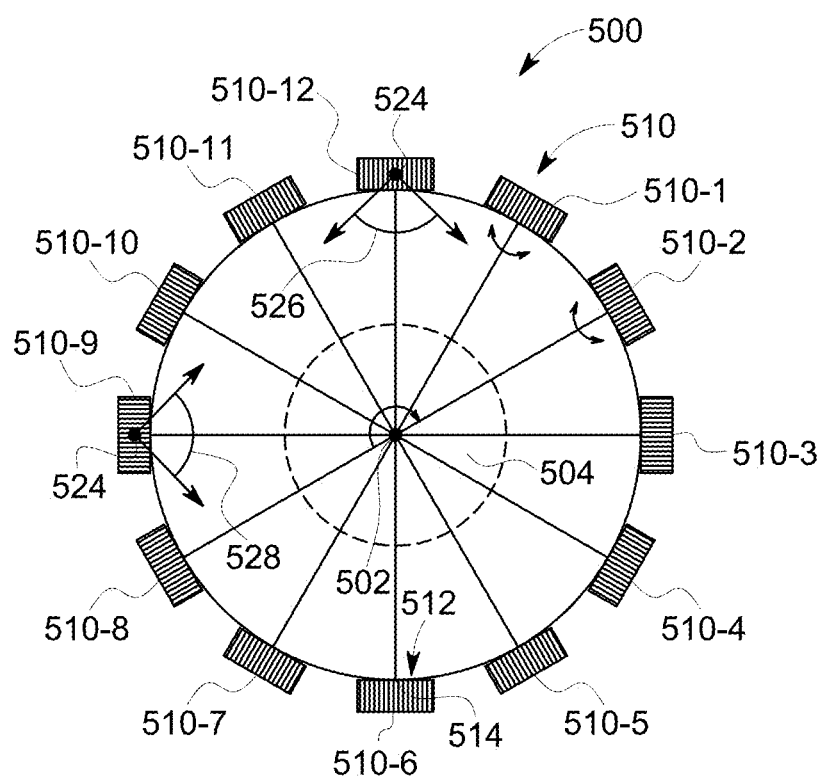
FIG. 4 illustrates an imaging arrangement of detector units in accordance with an embodiment.
Figure 5:
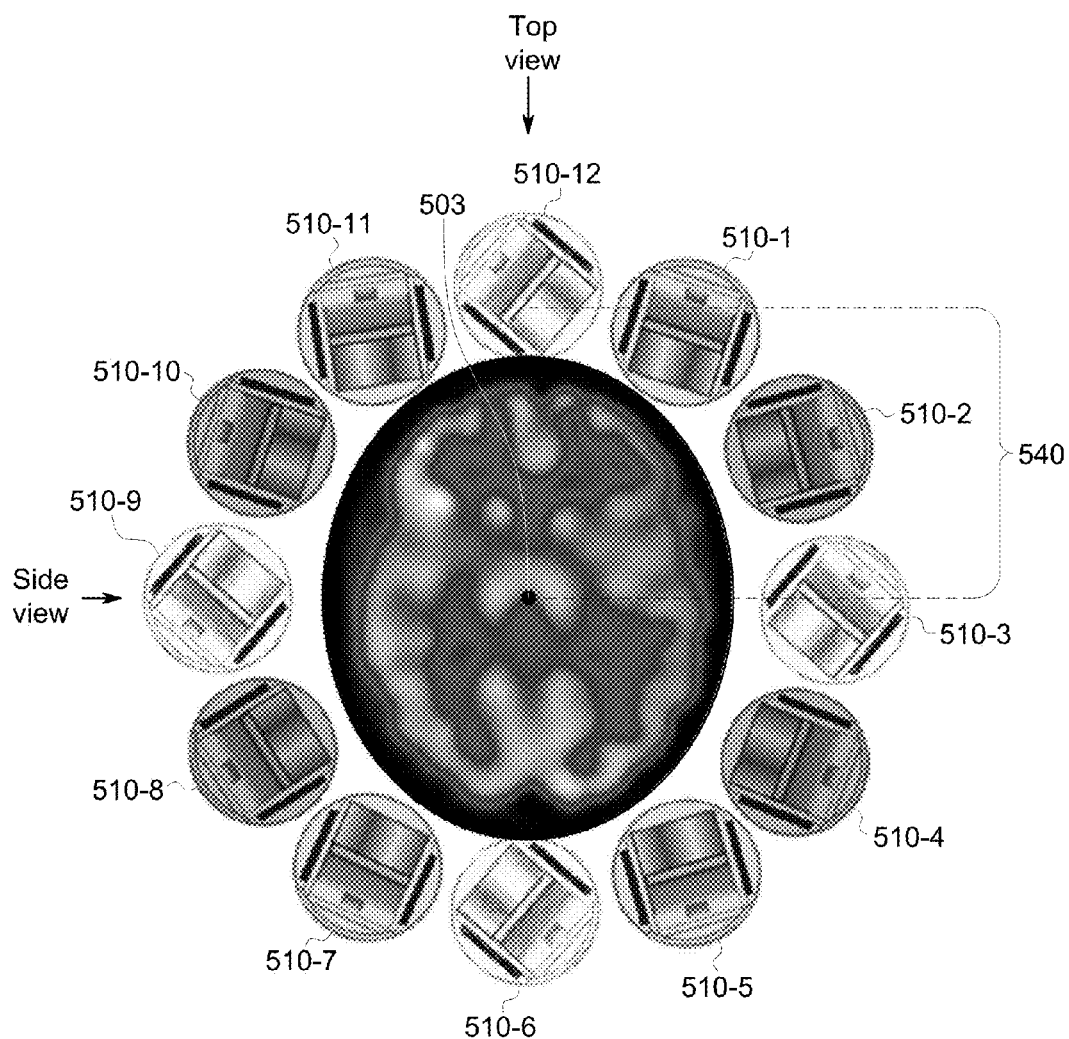
FIG. 5 illustrates the imaging arrangement of FIG. 4 in which the detector units have been positioned for brain persistence imaging.

FIG. 4 illustrates an imaging arrangement 500 of an imaging system (not shown) formed in accordance with an embodiment, and FIG. 5 depicts the imaging arrangement 500 being used for persistence imaging of a brain. The imaging system may be generally similar in various aspects to the imaging systems depicted and discussed in connection with FIGS. 1-3. As shown, a central longitudinal axis 502 extends into and out of the page. The longitudinal axis 502 may extend lengthwise through a center of a bore 504 (indicated by dashed line) of a gantry (not shown). The imaging arrangement 500 includes a plurality of detector units 510. Each of the detector units 510 includes a detection or acquisition surface 512 and a collimator 514.

Embodiments set forth herein include imaging arrangements in which a select number (e.g., less than all and/or less than a number of detector units that will be used for diagnostic image data acquisition) of the detector units are configured to acquire panoramic image data of the object. Based on the panoramic image data, a technician (or automated system) may position the object within the bore. The detector units 510 of the illustrated embodiment include 12 detectors, each labeled 510-"x", with the "x" denoting a position of a clock corresponding to the particular detector position. For example, the imaging arrangement 500 includes a first detector unit 510-12 (at a 12 o'clock or 0° position) and a second detector unit 510-9 (9 o'clock or 270° position). As seen in FIGS. 4 and 5, the first detector unit 510-12 and second detector unit 510-9 have substantially perpendicular positions with respect to each other. Accordingly, the first and second detector units 510-12 and 510-9 have substantially perpendicular positions with respect to each other and the longitudinal axis 502.

Due to the different positions with respect to the longitudinal axis 502, the first and second detector units 510-12, 510-9 may obtain image data along different anatomical planes. For example, the first detector unit 510-12 may acquire a coronal panoramic image (or top view), and the second detector unit 510-9 may acquire a sagittal panoramic image (or side view). Such embodiments may be particularly suitable for persistence imaging of ROIs having smaller volumes, such as ROIs that include the head or brain.

Each of the detector units (e.g., first and second detector units 510-12, 510-9) is configured to be rotated about a respective unit axis 524 and acquire image data as the detector units 510 are rotated. For example, the detector units 510 may be incrementally rotated within sweep ranges (e.g., sweep range 526 for the first detector unit 510-12 and sweep range 528 for the second detector unit 510-9). One or more projections may be obtained at each rotational position. This may be similar to a step-and-shoot process. For instance, the first detector unit 510-12 may be rotated from one rotational position to a subsequent rotational position. The rotational positions may differ by a designated angle, such as 6.7°. When the first detector unit 510-12 is stationary at a designated rotational position, the first detector unit 510-12 may acquire image data that is processed into a corresponding projection. The first detector unit 510-12 may then be rotated to the next rotational position. The next rotational position may differ from the previous rotational position by the same angle (e.g., 6.7°) or by a different angle. The designated angle or angles may be based on the size of the ROI and a number of desired projections. For example, the number of desired projections may be a number that is suitable for determining whether the ROI is properly positioned. Accordingly, a series or set of projections may be obtained that includes at least one projection from each rotational position. As an example, each of the rotational positions may differ from the prior or subsequent rotational position by 6.7°. A total of 14 projections may be acquired. In such an example, the sweep range is 94°. The second detector unit 510-9 may be operated in a similar or identical manner to acquire a series of projections at different rotational positions. Thus, embodiments may acquire one or more series or sets of projections. In FIGS. 4 and 5, for example, the detector unit 510-12 may obtain a coronal panoramic set of projections, and the detector unit 510-9 may obtain a sagittal panoramic set.

In some embodiments, one or more persistence images may be generated using less than all available detectors, or less than a number of detectors used for diagnostic imaging. With reference to FIGS. 4 and 5, in some embodiments only the first detector unit 510-12 and the second detector unit 510-9 may be used to acquire persistence image data, but at least some of the other detector units in addition to the first detector unit 510-12 and the second detector unit 510-9 may be used to acquire diagnostic image data used for reconstruction of a diagnostic image. For example, first persistence image data may be collected using the first detector unit 510-12 and second persistence image data may be collected using the second detector unit 510-9. A lateral positioning persistence image (see, e.g., FIG. 6) may be generated using the first persistence image data and an up-down positioning persistence image (see, e.g., FIG. 7) may be generated using the second persistence image data.

Figure 6:
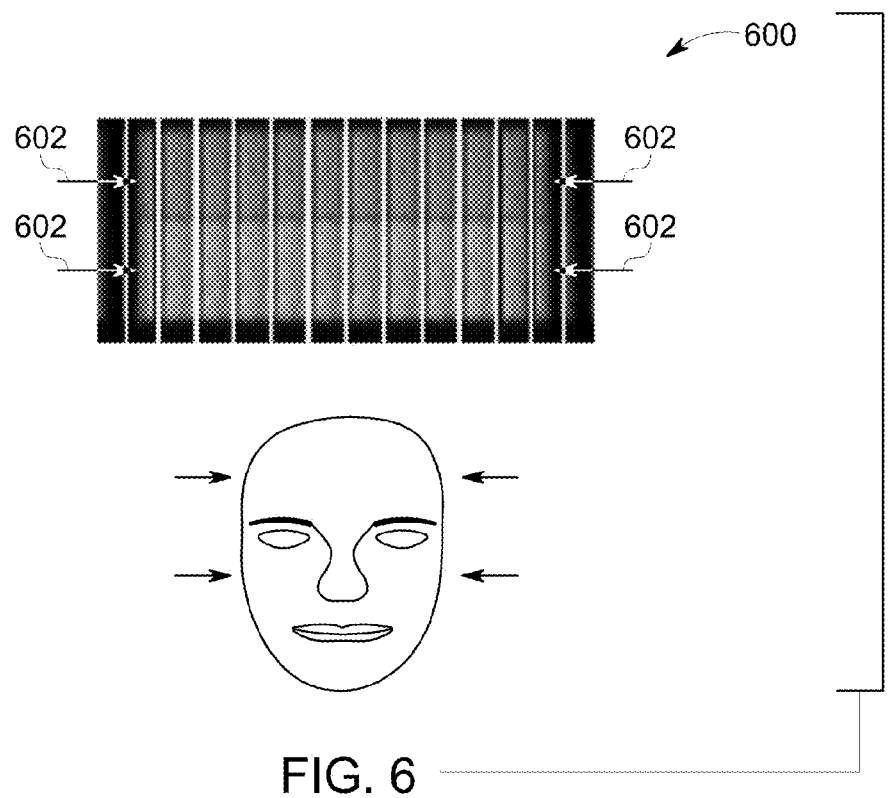
FIG. 6 illustrates a persistence image for lateral positioning in accordance with an embodiment.

FIG. 6 illustrates an example lateral positioning persistence image 600 (e.g., formed using first persistence image data collected using the first detector 510-12 only). As seen in FIG. 6, edges 602 of radiotracer activity may be observed and used to determine if the object is satisfactorily positioned laterally. For example, if the distance 540 (see FIG. 4) from the center of the bore to the reception surface of the first detector unit 510-12 is 17 centimeters, and 2 centimeter wide sections are acquired at each step of rotation of the first detector unit 510-12, the view step may be understood as 6.7° (as $\tan^{-1}$ (2 cm/17 cm)=6.7°). 14 views or projections are shown in FIG. 6 corresponding to a sweep range of 94° at 14 steps of 6.7° each. More or less steps, larger or smaller sweep ranges, and/or larger or smaller sweep steps may be employed in various embodiments. Further, as discussed herein, the sweep steps may vary in collection of data for a given persistence image (e.g., smaller sweep steps at the edges). The lateral positioning persistence image 600 may be utilized to determine if an object is appropriately laterally positioned and/or for making any appropriate adjustments to correct a lateral positioning of the object.

Figure 7:
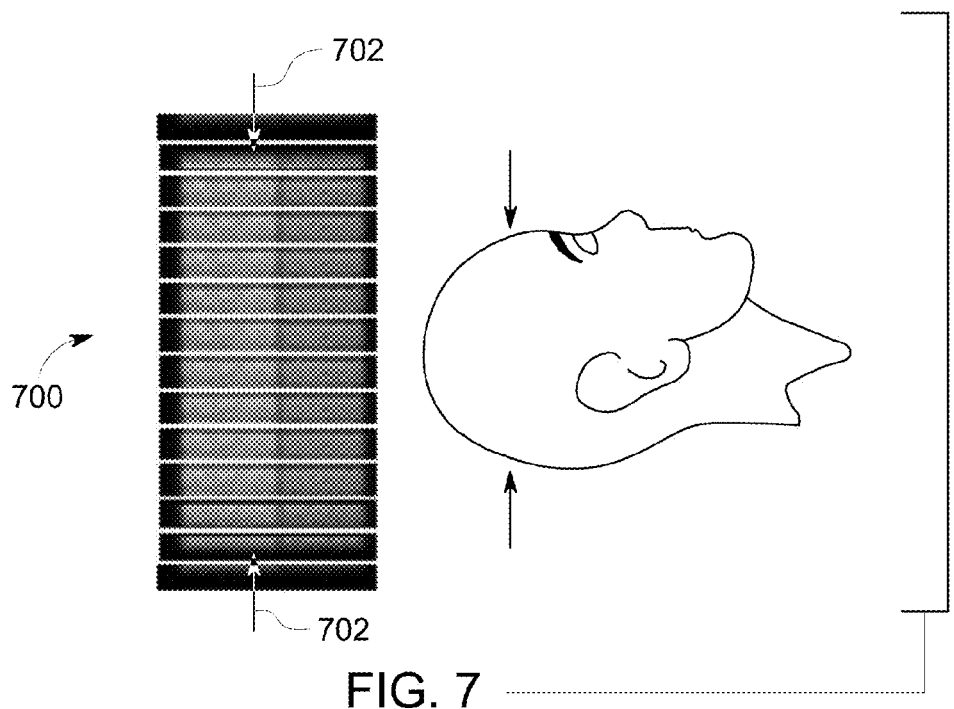
FIG. 7 illustrates a persistence image for up-down positioning in accordance with an embodiment.

FIG. 7 illustrates an example up-down positioning persistence image 700 (e.g., formed using second persistence image data collected using the second detector 510-9 only). As seen in FIG. 7, edges 702 of radiotracer activity may be observed and used to determine if the object is satisfactorily positioned in an up-down direction. The second detector 510-9 may be swept over a comparable range as the first detector 510-12, or may be swept differently than the first detector 510-12, as appropriate based on the size and shape of the object to be positioned. The up-down positioning persistence image 700 may be utilized to determine if an object is appropriately positioned in an up/down direction and/or for making any appropriate adjustments to correct an up-down positioning of the object (e.g., raising or lowering a table that supports the object).

It may be noted that additional detector units may be utilized to acquire persistence image data in various embodiments. For example, with continued reference to FIGS. 4-7, in some embodiments, a third detector unit 510-6 may be opposed to the first detector unit 510-12 (e.g., positioned on an opposite side of the object with a line of sight between the third detector unit 510-6 and the first detector unit 510-12 passing through the center of the bore). Similarly, a fourth detector unit 510-3 may be opposed to the second detector unit 510-9 (e.g., positioned on an opposite side of the object with a line of sight between the fourth detector unit 510-3 and the second detector unit 5109 passing through the center of the bore). Third persistence image data from the third detector unit 510-6 may be used (e.g., in combination with the first persistence image data from the first detector unit 510-12) to generate the lateral positioning persistence image (see, e.g., FIG. 6), and fourth persistence image data from the fourth detector unit 510-3 may be used (e.g., in combination with the second persistence image data from the second detector unit 510-9) to generate the up-down positioning persistence image (see, e.g., FIG. 7). Use of additional detectors for acquiring the persistence image data may allow individual detectors to cover shorter ranges, reduce an amount of time of persistence image data acquisition (e.g., two detectors may acquire an equivalent amount of data in half the time as one detector), and/or to increase the amount of information acquired for improved resolution or determination of positioning.

Figure 8:
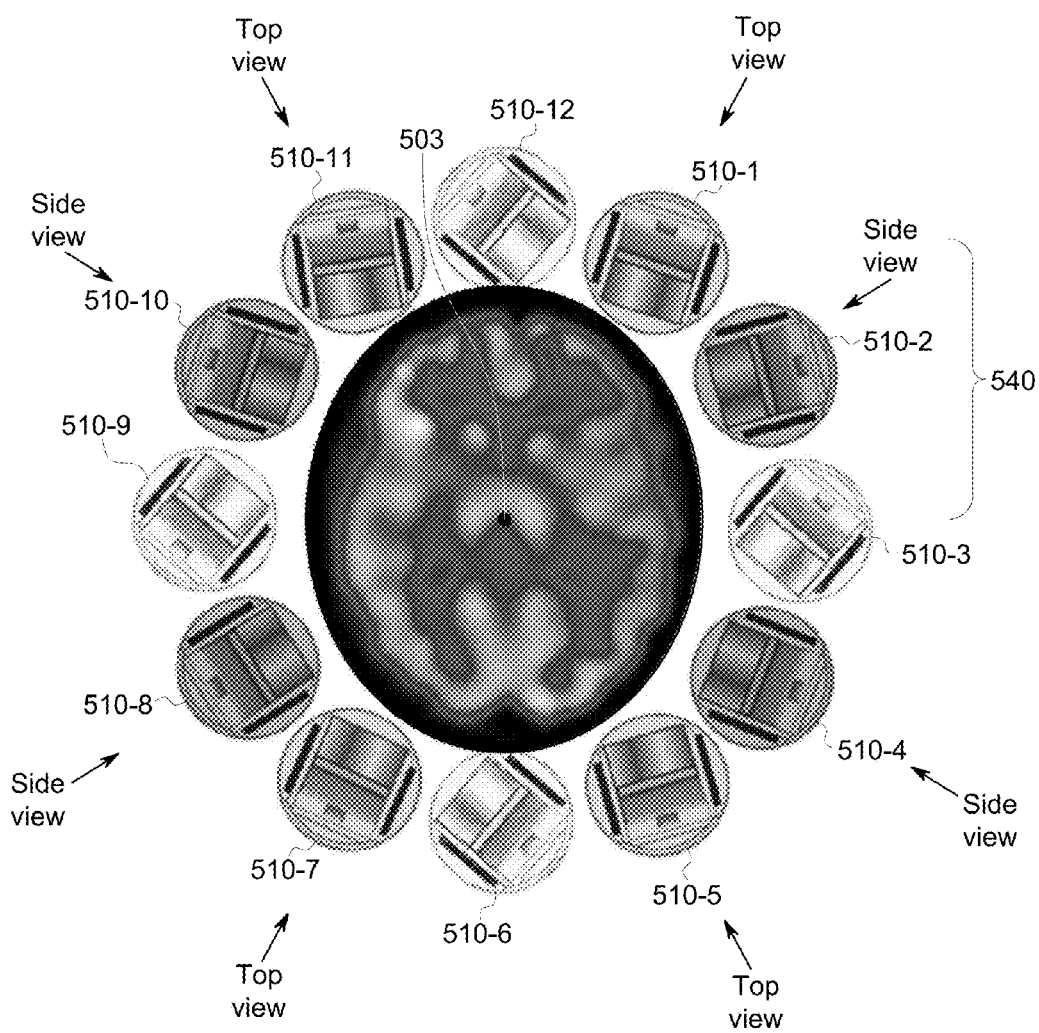
FIG. 8 illustrates an additional imaging arrangement of FIG. 4 in which detector units have been positioned for brain persistence imaging.

In some embodiments, additional or different detector units may be employed to collect persistence image data. For example, FIG. 8 depicts another example of the imaging arrangement 500 being used for persistence imaging of a brain. In FIG. 8, 2 sets of four detectors are used to acquire persistence imaging data. Each set of four detectors may include 2 opposed detectors. For example, in the illustrated example, detector units 510-1, 510-5, 510-7, and 510-11 (510-1 and 510-7 are opposed, and 510-5 and 510-11 are opposed) may be used to acquire persistence image data for generating a lateral positioning image data. Similarly, the depicted detector units 510-2, 510-4, 510-8, and 510-10 (510-2 and 510-8 are opposed, and 510-4 and 510-10 are opposed) may be used to acquire persistence image data for generating an up-down positioning image data. It may be noted that, in some instances, embodiments that use multiple detector units for a given persistence image may better locate a ROI having multiple anatomical structures that are desired to be imaged. For example, the separate kidneys of a patient may be more easily identified using one or more persistence images that are generated from image data of multiple detector units. Such embodiments may also decrease the time necessary to position the patient by acquiring the data for the persistence images more quickly.

It may be noted that while lateral and up/down positioning persistence images have been discussed herein, alternative or additional orientations may also be imaged and/or positioned in various embodiments. For example, persistence images may be used for in/out positioning (e.g., along a length of the patient or along the longitudinal axis 502).

Figure 9:
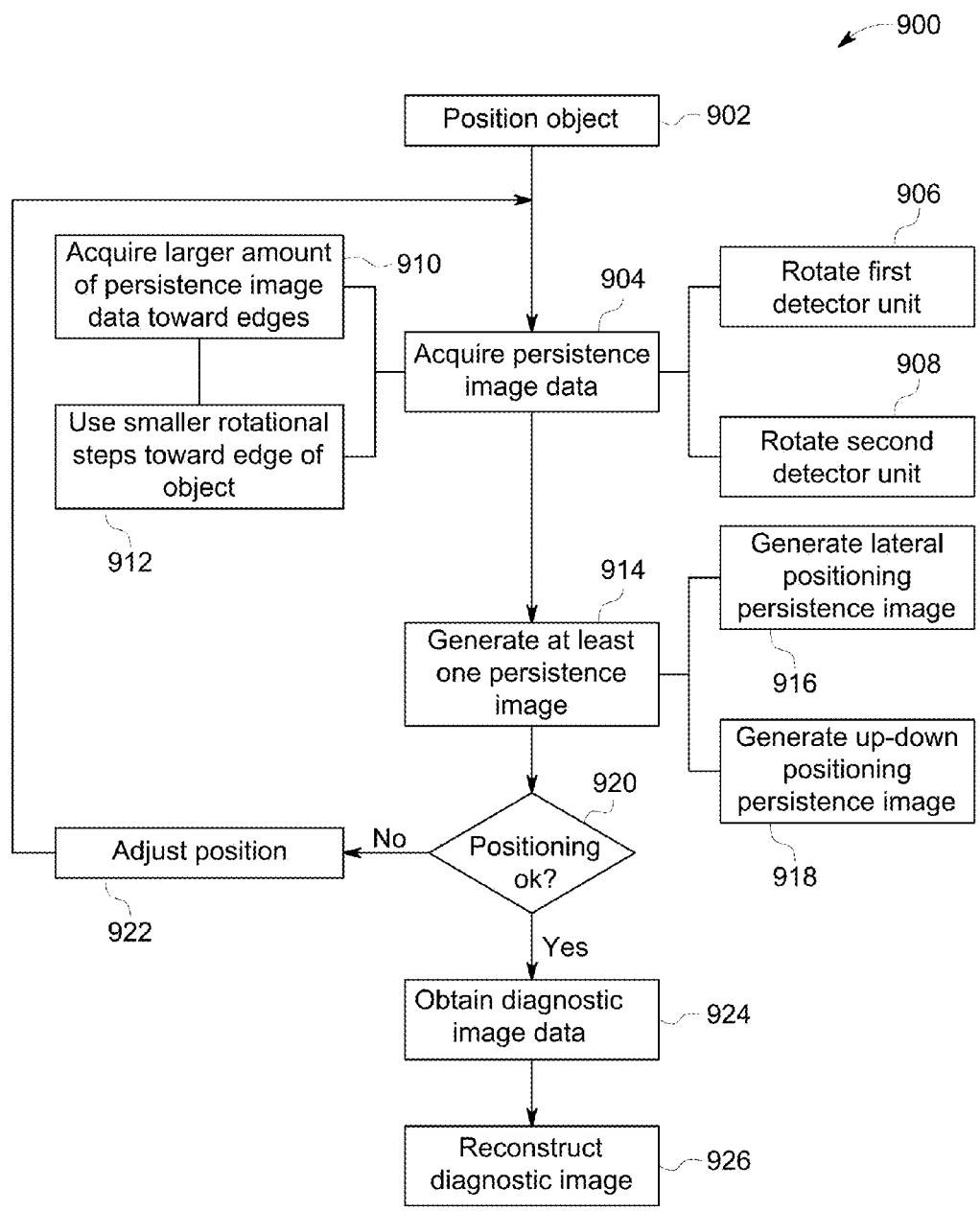
FIG. 9 shows a flowchart of a method in accordance with an embodiment.

FIG. 9 shows a flowchart of a method 900 in accordance with an embodiment. The method 900 may include, for example, positioning an object within a bore of an NM imaging system using persistence images obtained by the NM imaging system. The method 900 may be performed, at least in part, using the NM imaging system 100 and/or other aspects or components discussed herein. One or more steps of the method 900 may be performed by one or more processors of the NM imaging system (e.g., processing unit 150). One or more steps of the method 900 may also be based on user inputs. For example, a technician may use a remote control unit (RCU) that controls movement of the table. The technician may move the table based on one or more persistence images generated by the NM imaging system.

At 902, an object to be imaged is positioned. The object may be positioned in a bore of the NM imaging system, for example by being placed on a table that is then advanced into the bore.

At 904, persistence image data is acquired. For example, at 906 a first detector unit (e.g., a detector unit positioned at a 12 o'clock position with respect to the bore) may be rotated or swept over a range while used to acquire persistence image data. It may be noted that the first detector unit (or other detector unit) may be understood as rotating as used herein even if the detector unit is stationary during actual data acquisition, for example if the detector unit is temporarily stationary during a rotation or sweeping that is accomplished as a series of discrete steps. At 908, a second detector unit (e.g., a detector unit positioned at a 9 o'clock position with respect to the bore) may be rotated or swept over a range while used to acquire persistence image data. It may be noted that only one detector may be utilized in some examples, while more detectors may be used in others. In various embodiments, first persistence image data from the first detector (and/or other detectors) may be used to generate a first persistence image (e.g., a lateral positioning persistence image), while second persistence image data from the second detector (and/or other detectors) may be used to generate a second persistence image (e.g., an up-down positioning persistence image).

In some embodiments, the rotation or other aspect of one or more detectors may be varied during persistence image data acquisition. For example, in the illustrated example, at 910, a larger amount of persistence image data may be acquired toward one or more edges of the object (e.g., edges of radioactivity). It may be noted that information from the edges may be particularly useful in determining if an object is appropriately positioned, and thus, in various embodiments, persistence image data acquisition may emphasize collection of information at the edges over information toward the middle of the object to reduce overall persistence imaging acquisition time. In the illustrated embodiment, at 912, the first and second detector units may be moved incrementally to discrete rotational positions within corresponding sweep ranges, and smaller steps may be used between the rotational positions toward the edge of the object than toward the middle of the object for at least one of the first or second detector units. As another example, a rotational speed may be lower toward the edges than toward the middle for examples that acquire image data during a continuous sweep of detectors.

At 914, at least one persistence image is generated using persistence image data acquired at 904. For example, at 916, a lateral positioning persistence image is generated using persistence image data from a first detector, and at 918, an up-down positioning persistence image is generated using persistence image data from the second detector. In some embodiments, only the first and second detectors may be used to acquire persistence image data, while in other embodiments one or more additional or alternative detectors may be utilized to acquire persistence image data.

At 920, it is determined if the object is adequately positioned. If not, at 922, the position of the object is adjusted based on one or more persistence images. For example, if an up-down persistence positioning image indicates an object is positioned lower than desired, a table upon which the object is supported may be raised by an amount to correct the positioning. After the position is adjusted, the method 900 may return to 904 to acquire additional persistence image data to confirm whether the adjustment is sufficient to provide the object in a desired position or within an acceptable range of positions. If the position is determined to be adequate, the method 900 may next proceed to 924.

At 924, diagnostic image data is obtained. The diagnostic image data, in contrast to the persistence image data, is configured to be used to generate or reconstruct one or more diagnostic images having sufficient resolution or clarity to be used by a clinician in diagnosing the object (e.g., one or more organs or aspects of a patient). Accordingly, a substantially (e.g., ten times more) larger amount of information is collected as part diagnostic image data acquisition than persistence image information. As one example, more detector units may be employed for diagnostic image data acquisition than persistence image data acquisition. For instance, only the first and second detector units may be used for persistence image data acquisition, while the first, second, and additional detector units may be used for diagnostic image data acquisition. As additional examples, acquiring the diagnostic image data may include using at least one of additional sweep steps, a slower sweep rate, additional sweeps, a longer acquisition time, or a different energy window than used to acquire the persistence image data, as discussed herein. After collection of the diagnostic image data, at 926, a diagnostic image is reconstructed. The diagnostic image of the depicted embodiment has sufficient detail and resolution to be utilized by a clinician to diagnose a patient, in contrast to the persistence image(s) which were used only for positioning the patient.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a processor or a processing unit includes processing circuitry configured to perform one or more tasks, functions, or steps, such as those described herein. For instance, the processor may be a logic-based device that performs operations based on instructions stored on a tangible and non-transitory computer readable medium, such as memory. It may be noted that a "processor," as used herein, is not intended to necessarily be limited to a single processor or single logic-based device. For example, the processor may include a single processor (e.g., having one or more cores), multiple discrete processors, one or more application specific integrated circuits (ASICs), and/or one or more field programmable gate arrays (FPGAs). In some embodiments, the processor is an off-the-shelf device that is appropriately programmed or instructed to perform operations, such as the algorithms described herein.

The processor may also be a hard-wired device (e.g., electronic circuitry) that performs the operations based on hard-wired logic that is configured to perform the algorithms described herein. Accordingly, the processor may include one or more ASICs and/or FPGAs. Alternatively or in addition to the above, the processor may include or may be associated with a tangible and non-transitory memory having stored thereon instructions configured to direct the processor to perform the algorithms described herein.

It is noted that operations performed by the processor (e.g., operations corresponding to the methods/algorithms described herein, or aspects thereof) may be sufficiently complex that the operations may not be performed by a human being within a reasonable time period based on the intended application of the assay system. The processor may be configured to receive signals from the various subsystems and devices of the system or user inputs from the user. The processor may be configured to perform the methods described herein.

Processors may include or be communicatively coupled to memory. In some embodiments, the memory may include non-volatile memory. For example, the memory may be or include read-only memory (ROM), random-access memory (RAM), electrically erasable programmable read-only memory (EEPROM), flash memory, and the like. The memory may be configured to store data regarding operating parameters of the system 400.

In an exemplary embodiment, the processor executes a set of instructions that are stored in one or more storage elements, memories, and the like. Embodiments include non-transitory computer-readable media that include set of instructions for performing or executing one or more processes set forth herein. Non-transitory computer readable media may include all computer-readable media, except for transitory propagating signals per se. The non-transitory computer readable media may include generally any tangible computer-readable medium including, for example, persistent memory such as magnetic and/or optical disks, ROM, and PROM and volatile memory such as RAM. The computer-readable medium may store instructions for execution by one or more processors.

The set of instructions may include various commands that instruct the system to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) multi-head imaging system comprising:
   a gantry defining a bore configured to accept an object to be imaged;
   a plurality of detector units coupled to the gantry, each of the detector units having a respective detector field-of-view (FOV), each of the detector units configured to rotate about a respective unit axis, the plurality of detector units including at least a first detector unit and a second detector unit; and
   at least one processor configured to execute programmed instructions stored in memory, wherein the at least one processor, when executing the programmed instructions, performs the following operations:
      rotate the first detector unit and the second detector unit as the first and second detector units to acquire a first group of image data, the first group of image data configured to be used to adjust positioning, wherein the at least one processor is configured to acquire a larger amount of data toward the edge of the object than toward the middle of the object for at least one of the first or second detector units;
      generate at least one first image configured for use in positioning based on the first group of image data; and
      adjust a position of the object based on the at least one first image.

2. The NM imaging system of claim 1, wherein the first and second detector units are positioned at perpendicular positions about the bore.

3. The NM imaging system of claim 2, wherein the at least one processor is configured to use a first portion of the first group of image data from the first detector unit to generate a lateral positioning image and to use a second portion of the first group of image data from the second detector unit to generate an up/down positioning image.

4. The NM imaging system of claim 3, wherein the plurality of detector units further comprises a third detector unit opposed to the first detector unit, and a fourth detector unit opposed to the second detector unit, wherein the at least one processor is configured to rotate the third and fourth detector units, to use a third portion of the first group of image data from the third detector unit to generate the lateral persistence image and to use a fourth portion of the first group of image data from the fourth detector unit to generate the up/down positioning image.

5. The NM imaging system of claim 1, wherein each of the first and second detectors is rotated within a corresponding sweep range, the first and second detector units being incrementally moved to discrete rotational positions within the corresponding sweep range, wherein the at least one processor is configured to utilize smaller steps between the rotational positions toward the edge of the object than toward the middle of the object for at least one of the first or second detector units.

6. The NM imaging system of claim 1, wherein the plurality of detector units further comprises additional detector units, wherein the at least one processor is configured to use only the first and second detector units to acquire the first group of image data, to use the first, second, and at least some of the additional detector units to acquire a second group of image data after positioning the object based on the first group of imaging data, and to reconstruct a diagnostic image using the second group of image data.

7. The NM imaging system of claim 6, wherein the at least one processor is configured to acquire the second group of image data using at least one of additional sweep steps, a slower sweep rate, additional sweeps, or a longer acquisition time than used to acquire the first group of image data.

8. The NM imaging system of claim 6, wherein the at least one processor is configured to use a first energy window for acquiring the first group of image data and a second energy window for acquiring the second group of image data, wherein the first energy window is broader than the second energy window.

9. A method for acquiring image data of an object within a bore of a nuclear medicine (NM) multi-head imaging system, the NM imaging system comprising a plurality of detector units that are distributed about the bore and include a detector field-of-view (FOV), the plurality of detector units comprising at least a first detector unit and a second detector unit, the method comprising:
- rotating the first detector unit;
- rotating the second detector unit;
- acquiring a first group of image data with the first and second detector units while rotating the first and second detector units for use in positioning the object, wherein acquiring the first group of image data comprises acquiring a larger amount of data toward the edge of the object than toward the middle of the object for at least one of the first or second detector units;
- generating at least one first image for use in positioning the object using the first group of image data; and
- adjusting a position of the object based on the at least one first image.

10. The method of claim 9, wherein the first and second detector units are positioned at perpendicular positions about the bore.

11. The method of claim 10, further comprising:
- using a first portion of the first group of image data from the first detector unit to generate a lateral positioning image; and
- using a second portion of the first group of image data from the second detector unit to generate an up/down positioning image.

12. The method of claim 11, wherein the plurality of detector units further comprises a third detector unit opposed to the first detector unit, and a fourth detector unit opposed to the second detector unit, to the method further comprising:
- rotating the third and fourth detector units to acquire respective third and fourth portions of the first group of image data;
- using the use third portion of the first group of image data from the third detector unit to generate the lateral positioning image; and
- using the fourth portion of the first group of image data from the fourth detector unit to generate the up/down positioning image.

13. The method of claim 9, wherein each of the first and second detectors is rotated within a corresponding sweep range, the first and second detector units being incrementally moved to discrete rotational positions within the corresponding sweep range, wherein acquiring the first group of image data comprises utilizing smaller steps between the rotational positions toward the edge of the object than toward the middle of the object for at least one of the first or second detector units.

14. The method of claim 9, wherein the plurality of detector units further comprises additional detector units, the method further comprising:
- using only the first and second detector units to acquire the first group of image data;
- using the first, second, and at least some of the additional detector units to acquire a second group of image data after positioning the object based on the first group of imaging data; and
- reconstructing a diagnostic image using the second group of image data.

15. The method of claim 14, wherein acquiring the second group of image data comprises using at least one of additional sweep steps, a slower sweep rate, additional sweeps, a longer acquisition time, or a different energy window than used to acquire the persistence image data.

16. A tangible and non-transitory computer readable medium comprising one or more software modules configured to direct one or more processors to:
- rotate a first detector unit;
- rotate a second detector unit, wherein the first and second detector units are disposed about a bore of a gantry;
- acquire a first group of image data for use in a positioning an object being imaged with the first and second detector units while rotating the first and second detector units, wherein acquiring the first group of image data comprises acquiring a larger amount of data toward the edge of the object than toward the middle of the object for at least one of the first or second detector units;
- generate at least one first image using the first group of image data; and
- adjust a position of the object using the at least one first image.

17. The tangible and non-transitory computer readable medium of claim 16, wherein the first and second detector units are positioned at perpendicular positions about the bore.

* * * * *